US005713350A

United States Patent [19]

Yokota et al.

[11] Patent Number: 5,713,350
[45] Date of Patent: Feb. 3, 1998

[54] PATIENT INFORMATION ANALYSIS MANAGEMENT SYSTEM AND METHOD

[75] Inventors: Junichiro Yokota, Osaka-fu; Masayuki Ishimaru, Tokyo, both of Japan

[73] Assignee: Fukuda Denshi Kabushiki Kaisha, Tokyo, Japan

[21] Appl. No.: 708,537

[22] Filed: Sep. 5, 1996

[30] Foreign Application Priority Data

Sep. 6, 1995 [JP] Japan ................................ 7-228953

[51] Int. Cl.⁶ ................................................ G06F 15/42
[52] U.S. Cl. .......................... 128/630; 395/203; 128/710
[58] Field of Search ............................. 395/924, 934, 395/202, 203; 128/710, 712, 670, 630, 903, 904

[56] References Cited

U.S. PATENT DOCUMENTS

| | | | |
|---|---|---|---|
| 3,727,190 | 4/1973 | Vogelman et al. | 395/203 |
| 4,315,309 | 2/1982 | Coli | 395/203 |
| 4,857,716 | 8/1989 | Gombrich et al. | 128/903 |
| 5,265,010 | 11/1993 | Evans-Paganelli et al. | 128/630 |
| 5,291,399 | 3/1994 | Chaco | 395/203 |
| 5,301,105 | 4/1994 | Cummings, Jr. | 395/202 |
| 5,361,202 | 11/1994 | Doue | 395/203 |

*Primary Examiner*—William E. Kamm
*Assistant Examiner*—Kennedy J. Schaetzle
*Attorney, Agent, or Firm*—Merchant, Gould, Smith, Edell, Welter & Schmidt, P.A.

[57] ABSTRACT

In medical facilities in which medical treatments are performed at a plurality of locations, the state of a patient can be continuously and time-serially determined even if the location at which the medical treatment is given changes. Patient information collection systems for collecting medical treatment results of patients are installed in a plurality of locations where medical treatments are performed. A server system (800) capable of receiving information from each system and storing patient information is arranged. Every time the patient is moved from one room to another room, the destination is sent to the server system (800), and the server system can trace and store the patient information. Data collected from a patient and to be sampled and stored are temporarily displayed and confirmed by a physician or the like, and the confirmed data are specified as sampled data.

9 Claims, 22 Drawing Sheets

FIG. 10

PATIENT ATTRIBUTE INPUT

| VISITING INFORMATION | NURSING ATTRIBUTE | INPUT BY MAIN PHYSICIAN IN CHARGE | GRAVE DEGREE CALCULATION |
|---|---|---|---|

| | | | |
|---|---|---|---|
| PATIENT ID NUMBER | 27 | | |
| READING OF NAME OF PATIENT IN KANJI CHARACTER | | | |
| NAME OF PATIENT | | | |
| BIRTH OF DATE | 1967 | 3 | 4 |
| AGE | 27 | 7 | |
| SEX | MALE | | |
| HEIGHT | 167.8 cm | | |
| WEIGHT | 62.5 kg | | |
| BODY SURFACE AREA | 1.6998 m² | | |
| BLOOD TYPE | RH+A | | |
| RACE | ● YELLOW (JAPANESE)<br>○ YELLOW (OTHER THAN JAPANESE)<br>○ WHITE<br>○ BLACK<br>○ OTHERS | | |

TREATMENT 02

PAST HISTORY

☐ NONE

☒ DISEASE
- ☐ STROKE
- ☐ CHF/HEART FAILURE
- ☐ COLD
- ☐ HEPATIC CIRRHOSIS
- ☐ ALIMENTARY TRACT
- ☐ GENITAL SYSTEM
- ☐ MENTAL DISORDER
- ☐ MALIGNANT TUMOR
- ☐ HYPERTENSION
- ☐ RENAL INSUFFICIENCY
- ☐ DM
- ☐ OTHERS
- ☐ OTHER DISEASES OF CRANIAL NERVE SYSTEM
- ☐ OTHER DISEASES OF CARDIOVASCULAR SYSTEM
- ☐ OTHER DISEASES OF RESPIRATION SYSTEM
- ☐ OTHER DISEASES OF HEPATOCHOLEDOCHUS SYSTEM AND PANCREAS
- ☐ OTHER DISEASES OF RENAL AND URINARY SYSTEM
- ☐ OTHER DISEASES OF ENDOCRINE METABOLISM SYSTEM
- ☐ OTHER DISEASES OF MENTAL ABERRATIONS

☐ WOUND
- ☐ HEAD AND NECK
- ☐ LEGS AND ARMS
- ☐ CHEST
- ☐ OTHERS
- ☐ ABDOMEN

☒ SURGICAL OPERATION
- ☐ HEAD AND NECK
- ☐ LEGS AND ARMS
- ☒ CHEST
- ☐ DISEASE
- ☐ ABDOMEN

☒ BLOOD TRANSFUSION

☐ MEDICINE ALLERGY

☒ OTHERS (DRINKING, SMOKING, ETC.)

☐ PAST TRIAL OF SUICIDE

[CANCEL] [OK]

FIG. 11

| ITEM | 18:10 | CONFIRMATION | |
|---|---|---|---|
| HR | 0.00 | OK | NG |
| PR | 0.00 | OK | NG |
| RR | 0.00 | OK | NG |
| APS | 0.00 | OK | NG |
| APD | 0.00 | OK | NG |
| T1 | 0.00 | OK | NG |
| T2 | 0.00 | OK | NG |
| SpO2 | 0.00 | OK | NG |
| ICP | 0.00 | OK | NG |
| CVP | | OK | NG |
| | OK | | |
| | CANCEL | | |

PDMS  94/08/27  18:10:25

CONFIRMATION OF ON-LINE DATA

ANGIOGRAPHICAL ROOM

FIG. 13

| | NAME OF MEDICINE | POTENCY | VOLUME | USE COUNT | | | | |
|---|---|---|---|---|---|---|---|---|
| | (SELECTION FROM DICTIONARY) | (DICTIONARY DATA) | | (NUMERAL VALUE INPUT) | | ADMINISTRATION RATE | 100 ml/hr | |
| | | | | | | START TIME | 08:00 | |
| | | | | | A | B | C | D |
| BASIC INFUSION | MEDICINE 01 | 0mg | 500ml | 1A | | | | |
| ADJUVANT 1 | MEDICINE 02 | 100mg | 1ml | 1A | 1A | 1A | 1A | |
| ADJUVANT 2 | MEDICINE 03 | 500ug | 1ml | 1A | | | | |
| ADJUVANT 3 | MEDICINE 04 | 500mg | 2ml | 1A | | | | |
| ADJUVANT 4 | | | | | | | | |
| ADJUVANT 5 | | | | | | | | |
| ADJUVANT 6 | | | | | | | | |
| ADJUVANT 7 | | | | | | | | |
| ADJUVANT 8 | | | | | | | | |
| ADJUVANT 9 | | | | | | | | |
| TOTAL VOLUME | | | | | 504 ml | 501 ml | 502 ml | 501 ml |

FIG. 14

| | (SELECTION FROM DICTIONARY) | (DICTIONARY DATA) | | (NUMERAL VALUE INPUT) |
|---|---|---|---|---|
| | NAME OF MEDICINE | POTENCY | VOLUME | USE COUNT |
| BASIC MEDICINE | MEDICINE 01 | 500mg | 0ml | 1A |

| SOLVENT 1 | DISTILLED WATER | ---- | 20ml | NOTE 1 |
|---|---|---|---|---|
| | | TOTAL VOLUME | 20ml | NOTE 2 |

| ADMINISTRATION RATE | 10 ml/hr |
|---|---|
| START TIME | 08:00 |

FIG. 15

| | (SELECTION FROM DICTIONARY) | (DICTIONARY DATA) | | (NUMERAL VALUE INPUT) |
|---|---|---|---|---|
| | NAME OF MEDICINE | POTENCY | VOLUME | USE COUNT |
| BASIC MEDICINE | MEDICINE 01 | 500mg | 0ml | 1A |

| | | | |
|---|---|---|---|
| SOLVENT 1 | DISTILLED WATER | --- | 20ml |
| SOLVENT 2 | | | |
| SOLVENT 3 | | | |

NOTE

TOTAL VOLUME  20ml

| ADMINISTRATION INTERVAL | EVERY 10 MINUTES |
| ADMINISTRATION RATE | 1 min |
| START TIME | 08:00 |

FIG. 16

| | NAME OF NUTRIENT | POTENCY | VOLUME | USE COUNT |
|---|---|---|---|---|
| | (SELECTION FROM DICTIONARY) | (DICTIONARY DATA) | | (NUMERICAL VALUE INPUT) |
| NUTRIENT (INJECTION MEDICINE DICTIONARY) | NUTRIENT 01 | 100mg | 0ml | 1A |
| SOLVENT | WATER | | 20ml | |
| ADJUVANT | SALT | g | | |

TOTAL VOLUME  20ml

| ADMINISTRATION INTERVAL | EVERY 10 MINUTES |
|---|---|
| ADMINISTRATION RATE | 10  ml/hr |
| START TIME | 08:00 |

VERSION : 16.01

BED : ICU06
PATIENT ID NUMBER : 1004
NAME OF PATIENT : abcd
SEX :
BLOOD TYPE : RH+A ATTENTION ITEM:
- MEDICATION INTAKE
- RESTING LEVEL
- PYREXIA
- DISORDER
- ACHE
- INSOMNIA

| No | | NAME OF MEDICINE | | VOLUME | ADMINISTRATION RATE/TIME | TIME | REMARKS |
|---|---|---|---|---|---|---|---|
| 1 | ULTRA LOW VOLUME CONTINUOUS INTRAVENOUS DRIP INFUSION | MEDICINE 01 NORMAL SALINE SOLUTION 20ml | TOTAL | 1A 15ml 20ml | 16ml/hr | 11:02 | |
| 2 | ULTRA LOW VOLUME CONTINUOUS INTRAVENOUS DRIP INFUSION | MEDICINE 02 | TOTAL | 1A 200ml | 5ml/hr | 02:03 | |
| 3 | SHOT MEDICINE | MEDICINE 03 | | 1A | EVERY 24 HOURS | 01:24 | |
| 4 | SHOT MEDICINE | MEDICINE 04 NORMAL SALINE SOLUTION 20ml | TOTAL | 1A 20ml 20ml | EVERY 12 HOURS | 12:10 | |
| 5A | CONTINUOUS INTRAVENOUS DRIP INFUSION PATTERN A | MEDICINE 05 | TOTAL | 1A 160ml | 20ml/hr | 14:28 | |
| 6 | SHOT MEDICINE | MEDICINE 06 | | 1A 50ml | EVERY 12 HOURS | 17:03 | |
| 7 | ULTRA LOW VOLUME CONTINUOUS INTRAVENOUS DRIP INFUSION | MEDICINE 07 GLUCOSE 5% 20ml | TOTAL | 5A 48ml 48ml | 2ml/hr | 17:06 | |
| 8 | SHOT MEDICINE | MEDICINE 08 | TOTAL | 2A 0ml | EVERY 12 HOURS | 18:52 | |
| 9A | CONTINUOUS INTRAVENOUS DRIP INFUSION PATTERN A | MEDICINE 09 MEDICINE 10 GLUCOSE 50% 20ml | TOTAL | 1A 1A 5A 620ml | 80ml/hr | 01:32 | |
| 10 | ULTRA LOW VOLUME CONTINUOUS INTRAVENOUS DRIP INFUSION | MEDICINE 11 | TOTAL | 20A 20ml | 3ml/hr | 07:26 | |
| 11 | SHOT MEDICINE | MEDICINE 12 | TOTAL | 5A 0ml | EVERY 24 HOURS | 09:56 | |
| 12 | ULTRA LOW VOLUME CONTINUOUS INTRAVENOUS DRIP INFUSION | MEDICINE 13 NORMAL SALINE SOLUTION 20ml | TOTAL | 1A 40ml 50ml | 5ml/hr | 16:32 | |
| 13 | SHOT MEDICINE | MEDICINE 14 | TOTAL | 2A 0ml | EVERY 12 HOURS | 11:42 | |

5,713,350

1

PATIENT INFORMATION ANALYSIS MANAGEMENT SYSTEM AND METHOD

BACKGROUND OF THE INVENTION

The present invention relates to a patient information analysis management system having a patient information collection apparatus for collecting the results of medical treatments given to patients in a plurality of locations at which medical treatments are performed, in medical facilities for performing medical treatments at the plurality of locations, and a server apparatus capable of collecting and holding information from the patient information collection apparatus, and a method for the patient information analysis management system.

In a surgical operation for a patient in a hospital or the like, patient information is collected using a variety of monitor equipments, and the state of the patient is determined in accordance with various data collected by the monitor equipments, thereby managing the patient. These monitor equipments include a bed-side monitor for collecting, e.g., electrocardiogram information, a respiration gas monitor, and the like. A device for analyzing blood gases and electrolytes is also available as an emergency examination device.

These monitor equipments directly display the collected data or analyze them and display the analyzed data. An operating surgeon checks this display and performs a variety of necessary treatments.

Some monitor devices can record and temporarily store these collected data, and allow the operating surgeon to read out the data after the surgical operation, thereby checking any necessary portion.

These monitor equipments have display units unique to themselves and display information on the display units in accordance with the formats respectively unique to themselves. For example, an anesthetist or the like must check the display contents in entirely different formats of the equipments, instantaneously read the contents, and prepare a chart serving as a surgical operation record, thereby imposing a heavy load on the anesthetist or the like. In addition, the display contents have time shifts, and it is therefore difficult to analyze the display contents, taking the time shifts into account.

Although records including analysis results of various equipments in the operating room may be preserved, the collected data are rarely recorded when, for example, the patient is moved to an intensive care unit. When data is singly collected and recorded, the recorded data is part of the record of the patient, and the continuous state of the patient cannot be determined at all upon movement of the patient to another location for medical care. The patient's record is transmitted through only a document. This is also true for an emergency patient. The results of various examinations at the time of hospitalization are recorded in different formats with no connection between the respective examinations. The relationship between the examination results including the time factor is rarely recorded or analyzed.

Under these circumstances, a large number of examination results must be spread on a desk and compared with each other to diagnose illness. Strong demand has, therefore, arisen for a high-efficiency patient information management system.

SUMMARY OF THE INVENTION

The present invention has been made to solve the conventional problems described above, and has as its object to

2 provide a patient information analysis management system and method, in which the dispersed storage of patient information and collected data upon movement of a patient can be eliminated, these data are systematically managed as continuous information from the time when the patient is taken to the hospital to the time when the patient leaves the hospital, and the processing result can be output.

It is another object of the present invention to provide a patient information analysis management system and method, which are capable of managing the body fluid balance in infusion, blood transfusion, and the like, performing time-serial management and analysis of the correlation between various examinations and vital information, preventing errors in giving and receiving an instruction for a medical treatment, and improving nursing performance by reducing the amount of documents involved.

More specifically, the above object is to provide a patient information analysis management system and method, which continuously, time-serially store collected data upon giving medical treatments to a patient in different rooms after the patient visits a hospital to allow time-serial readout and output of vital information and various collected data of the patient without discontinuity, thereby providing a great help in diagnosing illness.

It is still another object of the present invention to provide a patient information analysis management system and method, in which patient data are checked and sampled every predetermined period of time instead of unconditionally sampling the patient data every predetermined period of time to become effective data so as to eliminate irrelevant data during collection, thereby storing high-precision collected data.

It is still another object of the present invention to provide a patient information analysis management system and method, which are capable of inputting information necessary for a medical treatment and the result of the medical treatment given to a patient from the input terminal of a patient's room upon movement of a patient to another room, and allowing a doctor to easily check the state of the medical treatment given to the patient.

A means for achieving the above objects has the following arrangement.

More specifically, a patient information analysis management system having a patient information collection apparatus for collecting results of medical treatments given to a patient in a plurality of locations at which medical treatments are performed, in a medical facility for performing medical treatments at the plurality of locations, and a server apparatus for collecting and holding information from the patient information collection apparatus, wherein the patient information collection apparatus comprises patient information transmitting means for transmitting the information of the results of the medical treatments taken by the patient to the server apparatus, display means for receiving the data transmitted to the server apparatus and displaying the received data on a display device, confirmation means for confirming display contents of the display means to output an instruction representing relevancy of the display contents, and informing means for informing the server apparatus of destination information when the medical treatment for the patient at a given location is completed and the patient moves to a next location, and the server apparatus comprises memory means capable of storing information necessary for medical treatments given to the patient and the results of the medical treatments taken by the patient, analysis return means for analyzing, as needed, the information transmitted from the patient information transmitting means of the patient information collection apparatus and returning an analysis result to the patient information collection apparatus, storage means for storing the information transmitted from the patient information transmitting means of the patient information collection apparatus and the analysis result from the analysis return means in the memory means, patient information control means for exchanging subsequent information associated with the patient with a patient information collection apparatus specified at a destination when the destination of the patient is sent from the informing means of the patient information collection apparatus, and confirmation information control means for accepting or discarding the display information, confirmed by the confirmation means of the patient information collection apparatus, in accordance with the confirmation result.

For example, the information sent by the patient information transmitting means of the patient information collection apparatus includes vital information collected from the patient and adjuvant information of the patient. The display means of the patient information collection apparatus can display data collected by the patient information collection apparatus. The data transmitted from the server apparatus, for example, includes adjuvant prescription information following an adjuvant prescription to the patient stored in the memory means in advance, and destination input guidance information at the informing means.

For example, the analysis return means of the server apparatus extracts patient measurement information for the predetermined period of time from the patient information transmitted from the patient information transmitting means and returns the extracted information as a sampling candidate, and the display means of the patient information collection apparatus displays the sampling candidate from the server apparatus and confirms storable information as measurement information from the sampling candidate information displayed on the display means. When the confirmation means instructs that the sampling candidate is irrelevant, the analysis return means of the server apparatus extracts new patient measurement information of the patient information transmitted from the patient information transmitting means and returns the new patient measurement information as a sampling candidate, and the display means of the patient information collection apparatus displays the sampling candidate retransmitted from the server apparatus, and the confirmation means checks if the retransmitted sampling candidate information displayed on the display means is storable information. When the confirmation means does not perform a confirmation operation for the predetermined period of time, the displayed sampling candidate is specified as the storable measurement information.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 10 is a view showing the patient attribute input window of the input terminal according to this embodiment;

FIG. 11 is a view showing the confirmation input window of sampling candidates according to this embodiment;

FIG. 13 is a view for explaining an instruction input when continuous intravenous drip infusion is selected as an item category in instruction file input processing according to this embodiment;

FIG. 14 is a view for explaining an instruction input when ultra low volume continuous intravenous drip infusion is selected as an item category in the instruction file input processing according to this embodiment;

FIG. 15 is a view for explaining an instruction input when a shot medicine is selected as an item category in the instruction file input processing according to this embodiment;

FIG. 16 is a view for explaining an instruction input when a nutrient is selected as an item category in the instruction file input processing according to this embodiment FIG. 17 is a view showing an example of the infusion/blood transfusion medicine input window of the input terminal according to this embodiment;

FIG. 20 is a view showing an example of the instruction file.

DETAILED DESCRIPTION OF THE PREFERRED EMBODIMENT

An embodiment according to the present invention will be described in detail with reference to the accompanying drawings.

Figure 1:
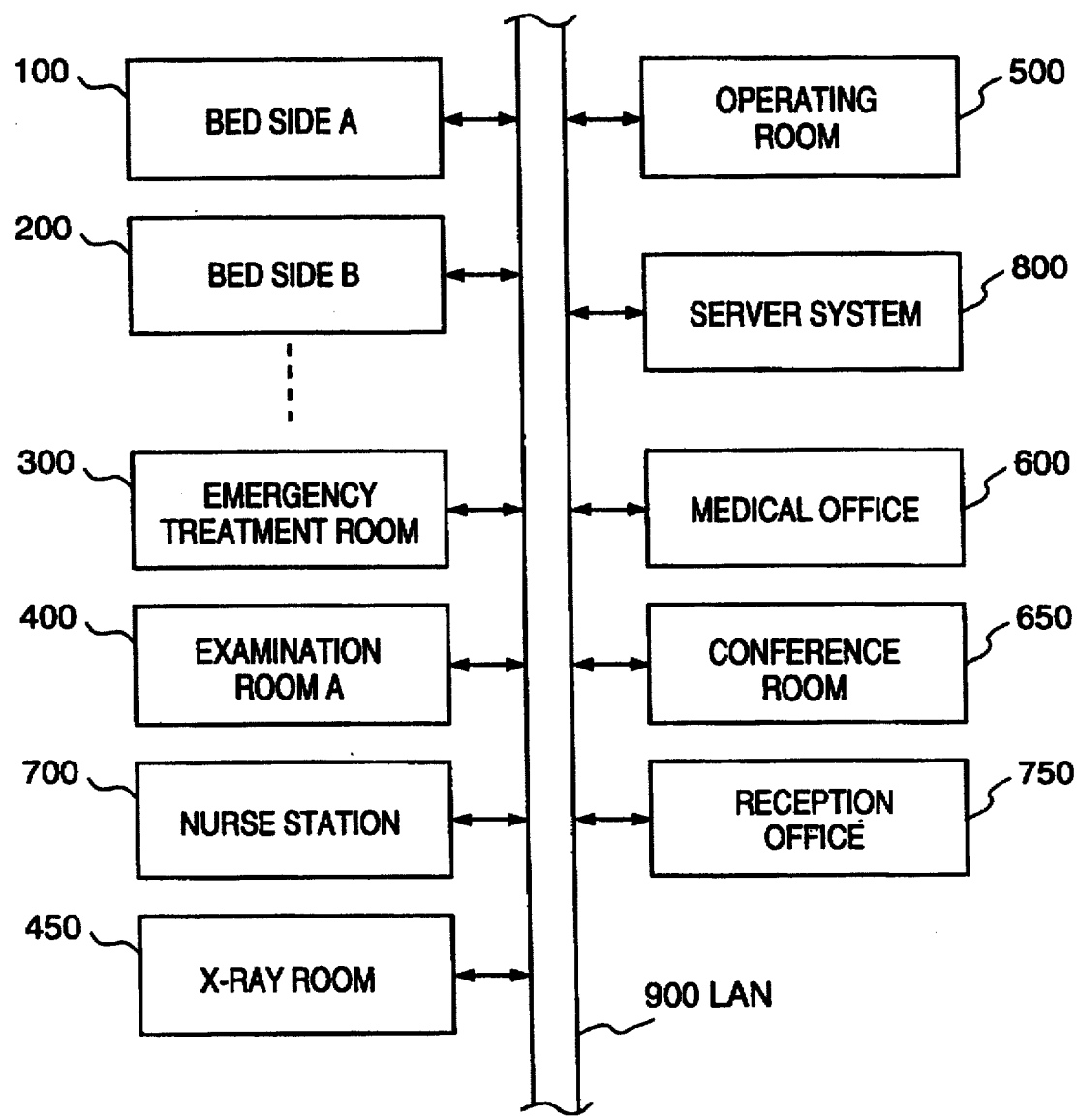
FIG. 1 is a block diagram showing a system configuration according to an embodiment of the present invention.

FIG. 1 is a block diagram showing the system configuration of a patient information analysis management system according to an embodiment of the present invention.

Referring to FIG. 1, reference numerals 100 and 200 denote patient information management systems on bed sides; 300, a patient information management system of an emergency treatment room (outpatient treatment room); 400, a patient information management system of a normal examination room (clinical examination room); 450, an X-ray room (CT room or angiographical room); 500, a patient information management system of an operating room; 600, a patient information management system of a medical office; 650, a conference room; 700, a patient information management system of a nurse station; 750, a reception office; and 800, a server system for collecting patient information from each system and analyzing it, and at the same time sending back the analysis results in a single format to the respective systems to cause the system to display the analysis results.

The systems are connected to each other through a network (LAN) 900. This network (LAN) 900 may be a known general network such as Ethernet or a network.

Figure 2:
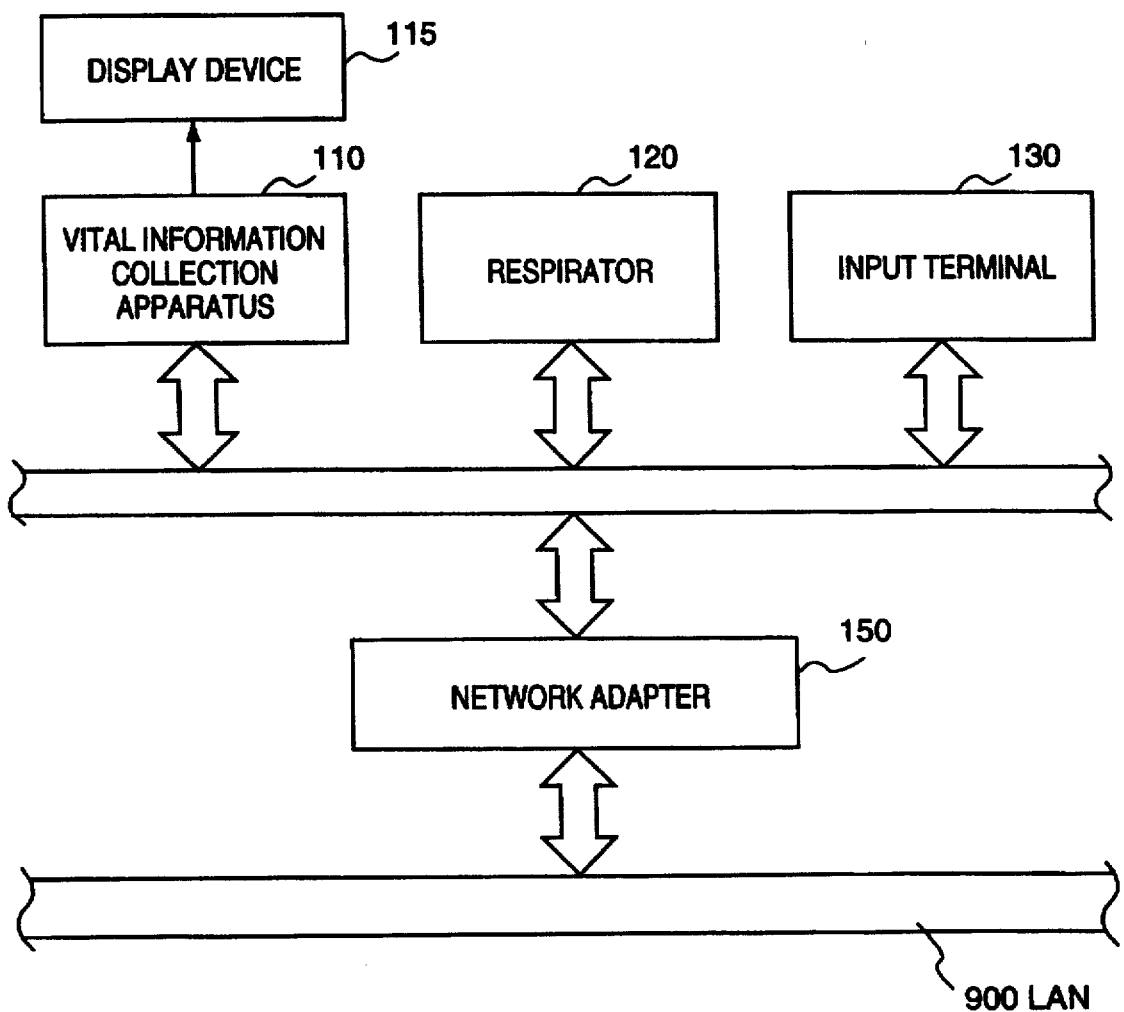
FIG. 2 is a detailed block diagram showing a bed-side system shown in FIG. 1 according to this embodiment.

The detailed arrangement of the patient information management system on the bed side shown in FIG. 1 is shown in FIG. 2. Referring to FIG. 2, the detailed arrangements of the emergency treatment room 300, the X-ray room 450, and the operating room 500 in addition to the bed side A 100 will be described. In the bed side A 100, reference numeral 110 denotes a vital information collection apparatus (bed-side monitor) for monitoring the vital signs of a patient on each bed. For example, the vital information collection apparatus 110 collects various kinds of information, e.g., the electrocardiogram, blood pressure, heart beat, and body temperature of each patient, and sends the collection results to the server system 800 through a network adapter 150. The apparatus 110 can analyze its own collection results and can send the analysis result to the server system 800 through the network adapter 150. In this embodiment, to reduce the communication traffic, the analysis result is transmitted in principle. The apparatus 110 can also receive data from the server system 800 and other systems through the network (LAN) 900 and the network adapter 150.

Reference numeral 115 denotes a display device capable of displaying various kinds of information under the control of the vital information collection apparatus 110 and can be constituted by, e.g., a CRT. Reference numeral 120 denotes a respirator; and 130, an input terminal obtained by integrally arranging a liquid crystal display 135 (to be described in detail later) and a touch panel.

The network adapter 150 has 8-channel input ports and controls interfacing with the network (LAN) 900 connecting various equipments connected to the input ports to other systems.

In the embodiment shown in FIG. 2, the input terminal 130 is directly connected to the network adapter 150. However, the present invention is not limited to this. The following arrangement may be employed in addition to the arrangement shown in FIG. 2. There is provided a personal computer system for receiving various kinds of information associated with a patient from the server system 800, performing predetermined processing for these kinds of information, and displaying the processed information on the display device. The input terminal 130 is connected to the personal computer. Information is input from a keyboard attached to the personal computer, if input operations are required. If no keyboard is used, information may be input from the input terminal 130. In this case, information displayed on the input terminal is simultaneously displayed on the display device attached to the personal computer. In addition, various kinds of patient information supplied from the server system 800 may be controlled to be displayed on the display device of the personal computer.

This personal computer can be exemplified by a Macintosh computer (e.g., a power Macintosh) available from Apple Computer.

The detailed arrangement of the system 400 of the examination room will be described in detail with reference to FIG. 3. Different types of patient information collection and examination apparatuses are often installed in different examination rooms. The arrangement is not limited to the one shown in FIG. 3. The same reference numerals as in FIG. 3 denote the same parts in FIG. 2, and a detailed description thereof will be omitted.

Figure 3:
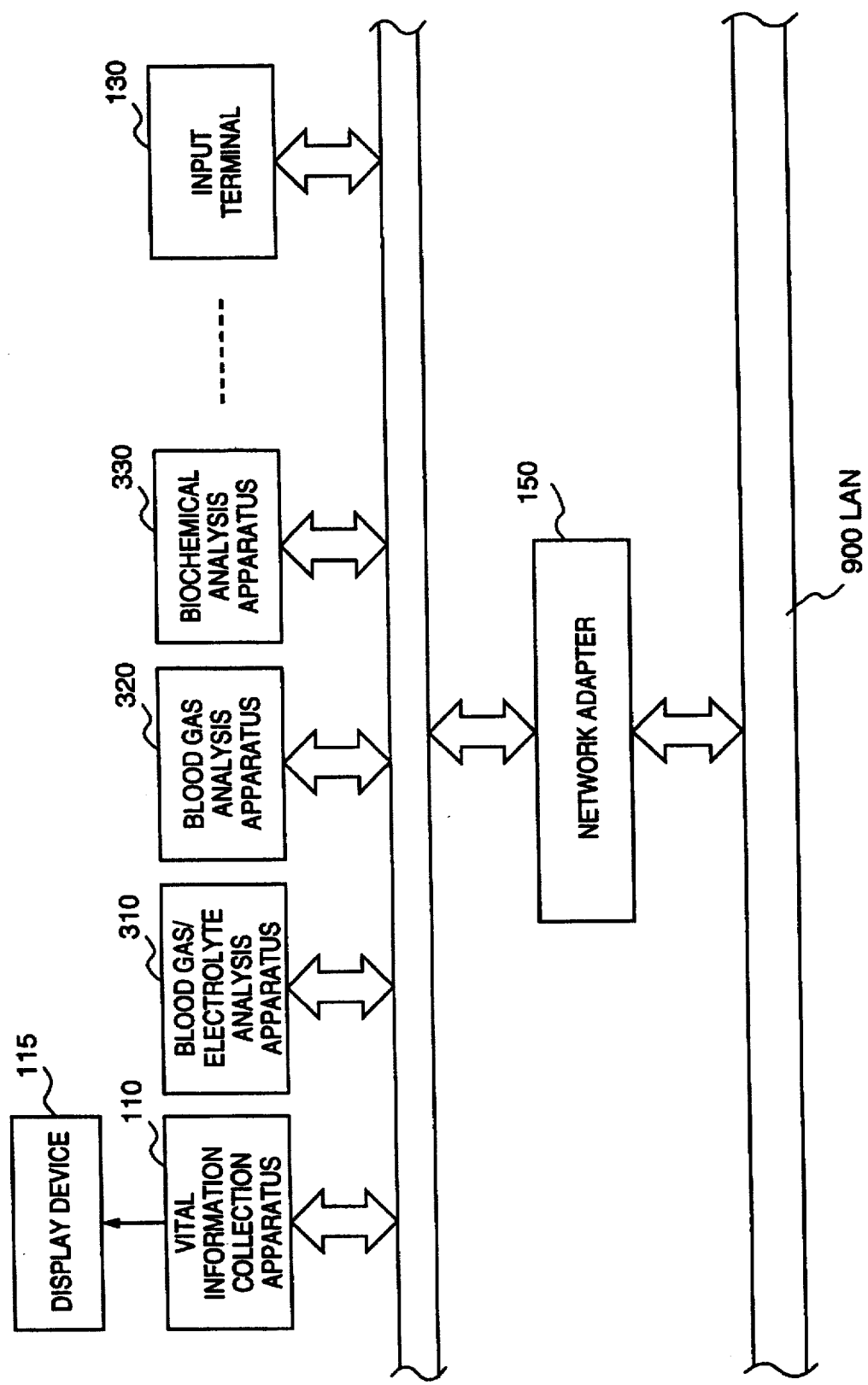
FIG. 3 is a detailed block diagram showing an examination room system shown in FIG. 1 according to this embodiment.

Referring to FIG. 3, reference numeral 310 denotes a blood gas/electrolyte analysis apparatus; 320, a blood gas analysis apparatus; and 330, a biochemical analysis apparatus. Other necessary patient collection/analysis apparatuses are connected through the network adapter 150 to exchange data, transmit various collection and analysis data to the server system 800 through the network (LAN) 900, and receive various instructions and display information from the server system 800.

The detailed arrangement of the medical office 600, the conference room 650, and the nurse station 700 will be described in detail with reference to FIG. 4. The same reference numerals as in FIG. 2 denote the same parts in FIG. 4, and a detailed description thereof will be omitted.

Figure 4:
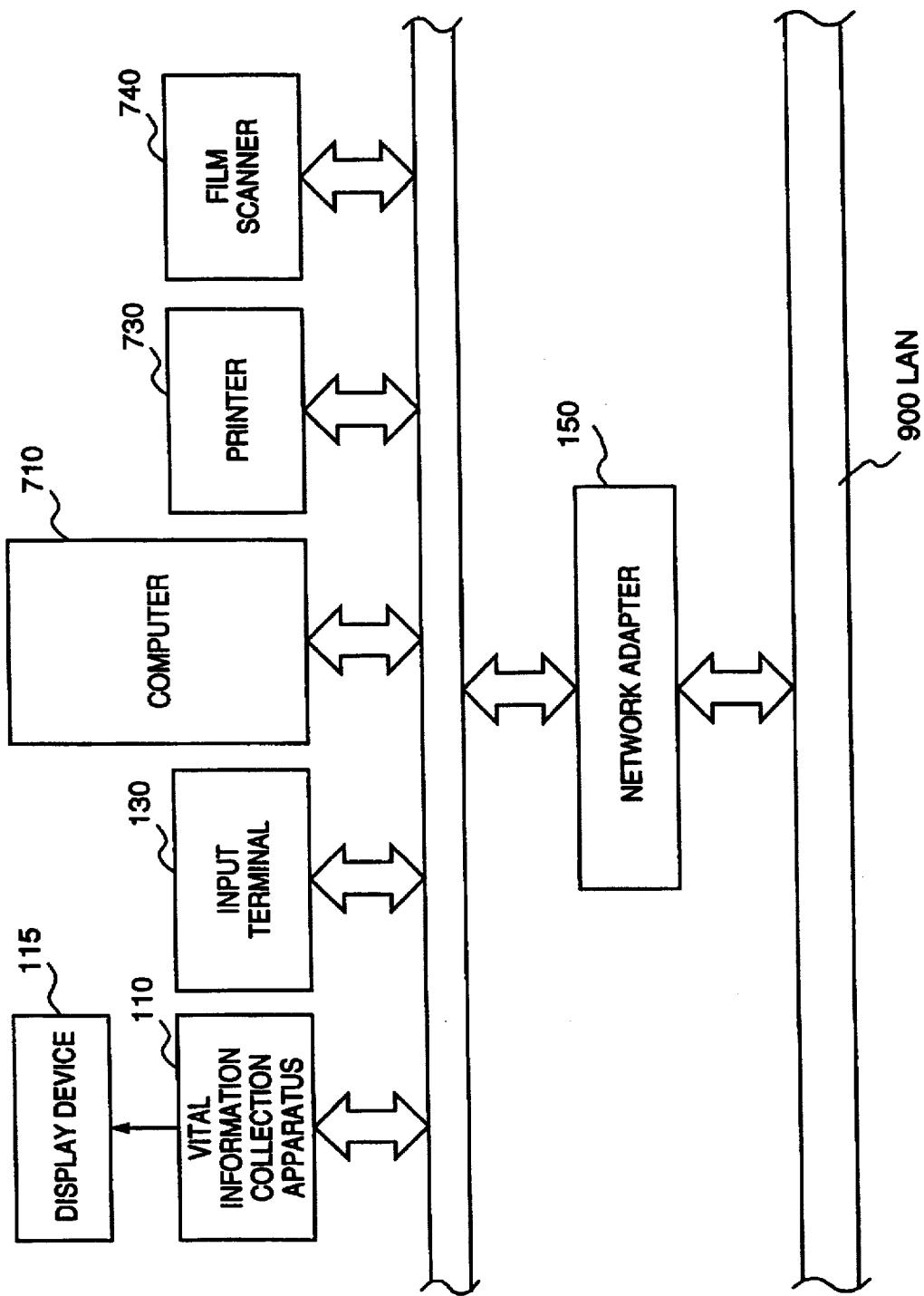
FIG. 4 is a detailed block diagram showing a nurse station system and a medicine office system shown in FIG. 1 according to this embodiment.

Referring to FIG. 4, reference numeral 710 denotes a computer having a display device and an operation panel. The computer 710 sends various instructions to each bed side and each examination room and can receive the states of each bed side and each examination room through the server system 800. The computer 710 then displays the reception contents on the display device to allow a physician to confirm the display contents, thereby managing each patient information.

Reference numeral 730 denotes a printer capable of printing out patient information. In this embodiment, the printer 730 comprises a laser beam printer. Reference numeral 740 denotes a scanner apparatus (film scanner) for reading image data such as a roentgenogram obtained by roentgenography and a UCG. This scanner 740 need not be arranged in the medical office 600, but is arranged in only the nurse station 700.

Since the system of each of the medical office 600 and the nurse station 700 includes the computer 710, various equipments are controlled under the control of the computer 710. A change in specifications can be easily coped with upon only a change in computer control. For this reason, the network adapter 150 may be omitted, and the computer 710 may be directly connected to the network (LAN) 900.

The detailed arrangement of the server system 800 will be described with reference to FIG. 5. The same reference numerals as in FIG. 2 denote the same parts in FIG. 5, and a detailed description thereof will be omitted.

Figure 5:
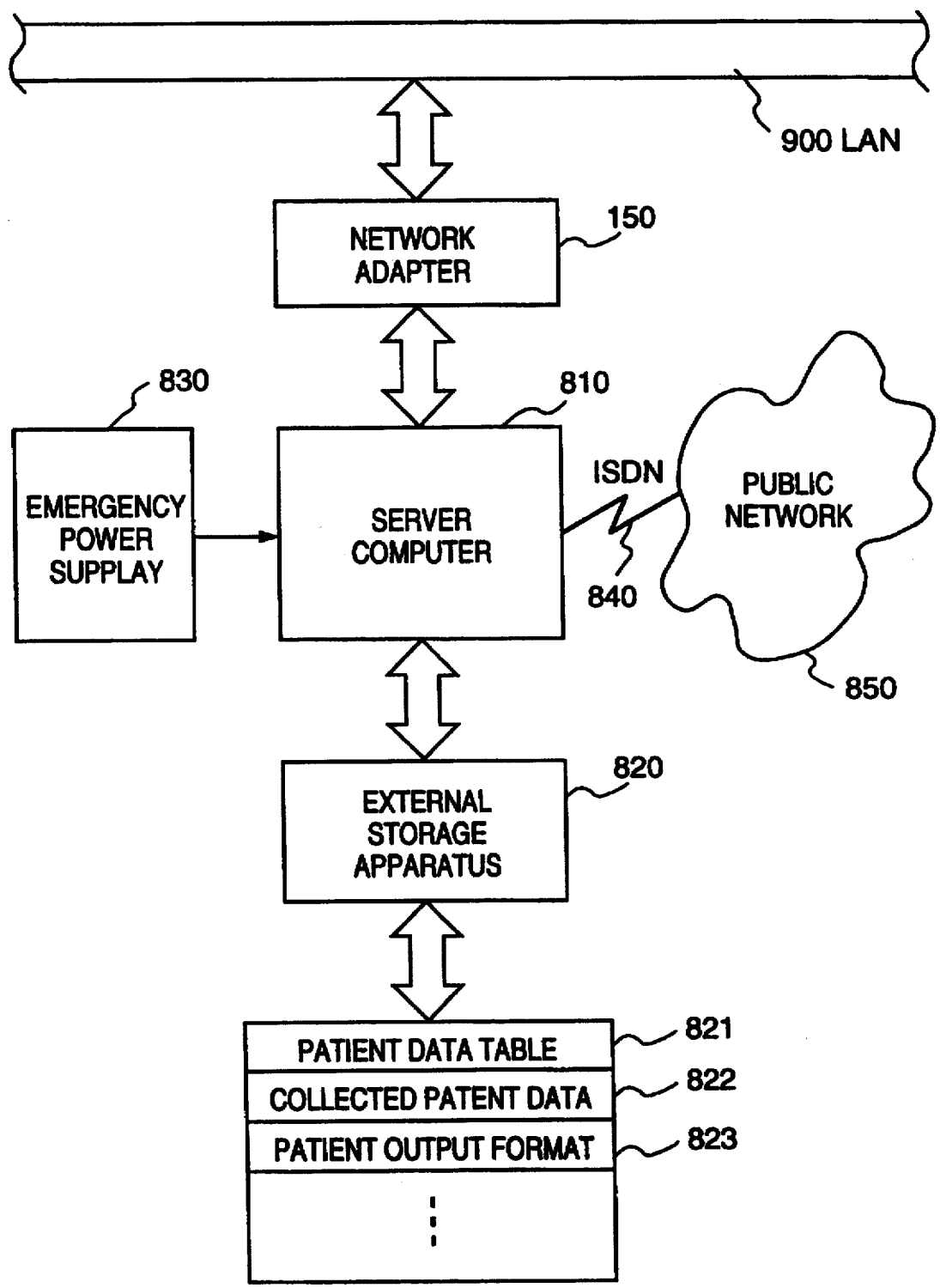
FIG. 5 is a detailed block diagram showing a server system shown in FIG. 1 according to this embodiment.

Referring to FIG. 5, reference numeral 810 denotes a server computer which comprises a high-performance UNIX machine in this embodiment. Reference numeral 820 denotes an external storage connected to the server computer 810. The external storage 820 stores patient information from the system of each room in a predetermined amount. Reference numeral 830 denotes an emergency power supply by which the stored patient information is protected from erasure even upon occurrence of an emergency such as a power failure.

Reference numeral 840 denotes an ISDN line for performing data communication with other digital equipments through another public network 850.

The storage area of the external storage 820 includes a patient data table area 821 for storing patient attribute data, a collected patient data storage area 822 for storing time-serial data collected from each patient at each treatment room or bed side, and a patient output format storage area 823 for storing an output format in printing out various analysis results of each patient. The storage area of the external storage 820 also includes an area for storing various treatment instruction data from the medical office for a patient.

The detailed arrangement of the above input terminal will be described with reference to FIG. 6.

Figure 6:
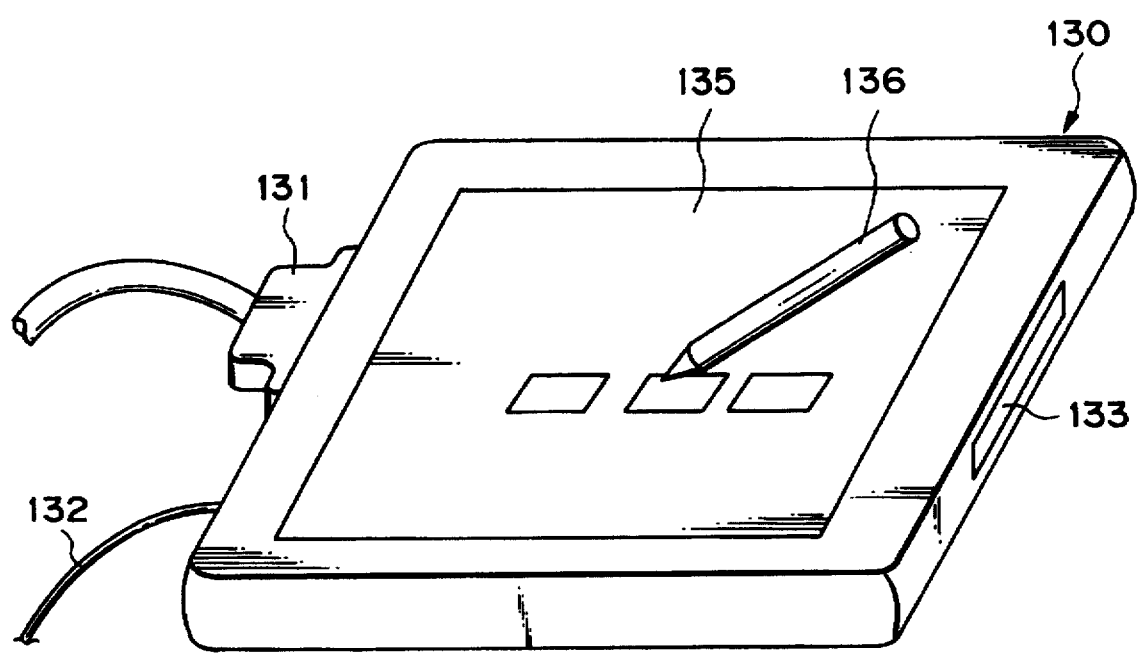
FIG. 6 is a perspective view showing the outer appearance of an input terminal according to this embodiment.

FIG. 6 is a perspective view showing the outer appearance of the above input terminal. The input terminal of this embodiment incorporates a CPU, a large-capacity hard disk, and a large-capacity memory. The input terminal has very low power consumption and can be battery-driven for a long period of time. In the input terminal 130 whose outer appearance is shown in FIG. 6 according to this embodiment, reference numeral 131 denotes a cable connected to the network adapter 150 and various computers; 132, a power cord; and 133, a connector for an expansion connector box. For example, a 3.5" flexible disk drive unit can be connected to the connector 133.

Reference numeral 135 in FIG. 6 denotes a liquid crystal display; and 136, an input pen. The display panel of the liquid crystal display 135 has a touch panel structure. Various software applications can be manipulated and numerals and characters can be input using display information on the liquid crystal display 135 and input coordinate positions designated with the pen 136.

Even an operator who cannot use a keyboard or is not accustomed to daily computer operations in a medical site can operate the input terminal 130 of this embodiment without causing troubles in medical treatments and nursing.

For example, the input terminal is a 98PEN having a large 9.8" liquid crystal display, available from NEC Corp. or a Thinkpad 360P having a large 9.8" liquid crystal display, available from IBM.

A processing flow in the system of an embodiment having the above arrangement and the display examples in the input terminal 130 and the display device 115 will be described below.

The system of this embodiment is a system suitable for use in a hospital or the like. At the time of hospitalization, the I.D. and name of a patient are input at the reception office 750. In examinations and treatments for, e.g., an emergency patient or a patient for whom a surgical operation is required, patient attributes are sequentially input from the computer 710 in the nurse station 700 or from the emergency treatment room 300. The input information is sequentially sent to the server system 800 to prepare a patient file together with the attributes of the patient in the server system 800. Various subsequent instruction inputs and collected information of this patient are stored in association with the prepared file.

Prior to the start of examinations and treatments for this patient, examination/treatment location data is designated and input. The server system 800 then recognizes that vital information sent from the designated location corresponding to the patient attribute previously designated. The server system 800 receives data for this patient and sends an analysis result, an instruction, and the like to the system installed in the designated location.

Predetermined treatments are sequentially performed in the corresponding rooms.

When the treatment is completed in a first room, the patient is moved to the next treatment room for a further treatment or to a bed because the patient must rest. In this embodiment, the destination of this patient is input, and various kinds of information on the patient are demanded to be sent from the system located at the currently designated position to that at a newly designated position.

When the patient reaches the newly designated destination, the server system 800 is notified of information representing that the patient has reached the newly designated position and various kinds of information to be sequentially sent from this position are of this patient. The collected patient information even during movement from the treatment room must preferably be sent to the server system 800 as much as possible. For example, if the system is connected to the server system 800 through radio communication, all the information during the movement is controlled to be sent to the server system 800 in real time. Therefore, an operation for collectively sending all the information, obtained during movement, upon arrival at the treatment room can be omitted.

In this embodiment, continuous information collection is allowed even if the treatment location of the patient changes. To continuously collect the patient information, only the destination, and the end of movement, if necessary, are input to continuously send the information of each patient to the server and stored therein without any special manipulation.

In addition to collection of patient information, when an instruction for a treatment for a patient is input in advance, the instruction can be sent to any location where the patient is present. An accurate and appropriate treatment can be given to the patient.

More specifically, in the system of this embodiment, treatments for the patient are input at the nurse station or medical office in advance, and the treatment contents can be displayed on the display unit of the input terminal at the time of actual treatments. Appropriate processing is performed upon confirmation of the display contents, and at the same time, a message representing that each actual treatment was given or is being given is input to prevent transmission errors in treatment instructions and treatment actions.

In this embodiment, patient information collected from the vital information collection apparatus or any other examination apparatus is sampled every predetermined period of time, and the sampled data is stored in the server system. In sampling vital information, the data collected from the vital information collection apparatus or any other examination apparatus can be directly stored every predetermined period of time. However, since the collected data may not be always relevant data, data to be sampled and stored is displayed on the display unit of the input terminal to prompt a confirmation input. If a confirmation input is made within a given period, the confirmed information is confirmed as storage data.

If the data displayed on the display unit is determined as irrelevant, collection of patient information is instructed again, and data sampled again is then confirmed.

All the above procedures are made. However, even if a confirmation input for given data is not made within the given period upon prompting the confirmation input, it is not suitable to omit the given data. In this embodiment, a flag representing that no confirmation input is made for given data is added to the given data, and the given data currently displayed on the display unit is stored as collected information of the given patient.

The above processing will be described in detail with reference to the flow charts of FIGS. 7 and 8.

When a patient such as an outpatient or emergency patient arrives at a hospital in step S1, and if the patient can input patient attributes, like an outpatient, the following pieces of information are input as many as possible in step S2. If the patient cannot input all his/her attributes, like an emergency patient, all possible attributes are preferably input.

Figure 9:
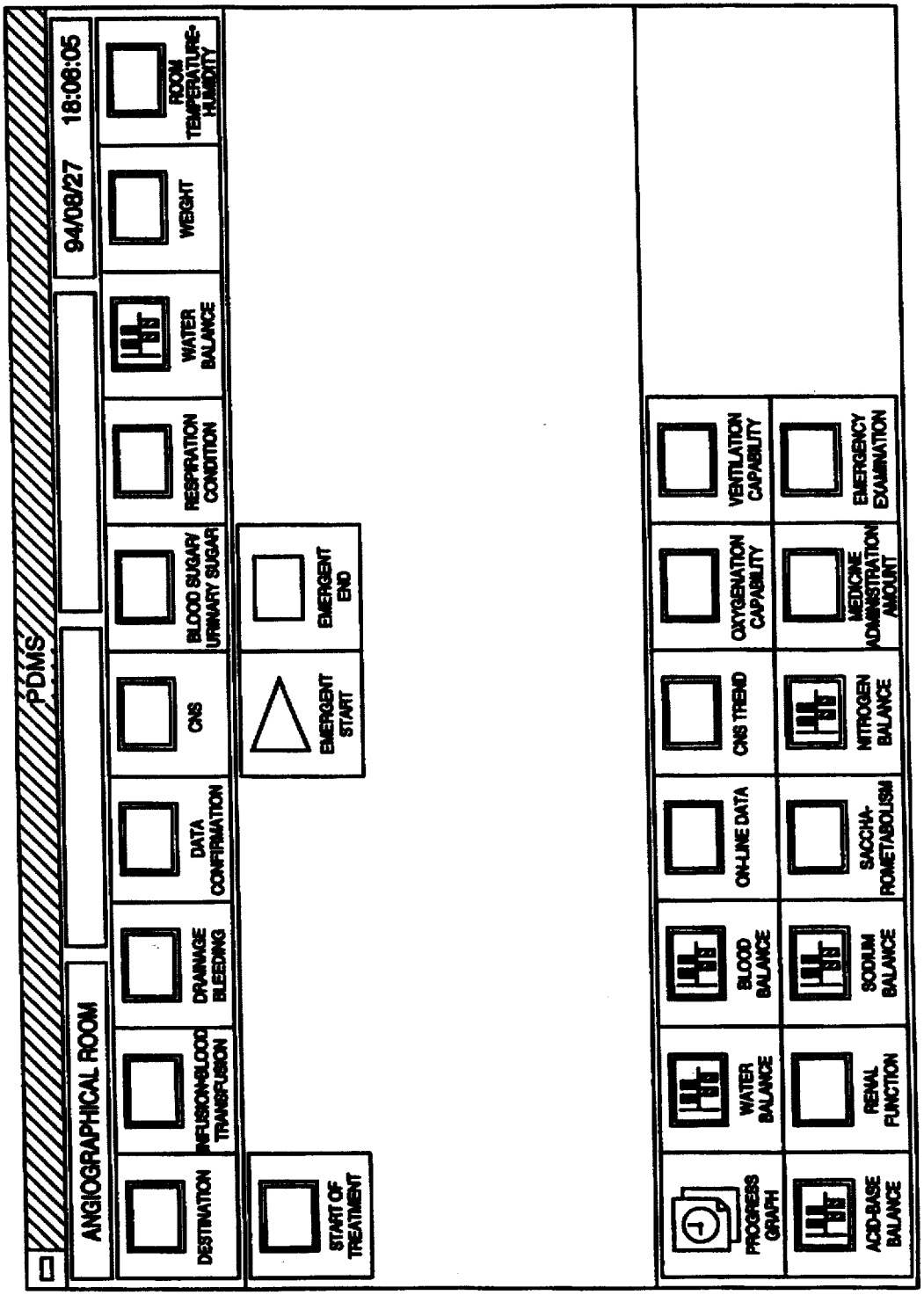
FIG. 9 is a view showing the initial menu window of the input terminal according to this embodiment.
Figure 12:
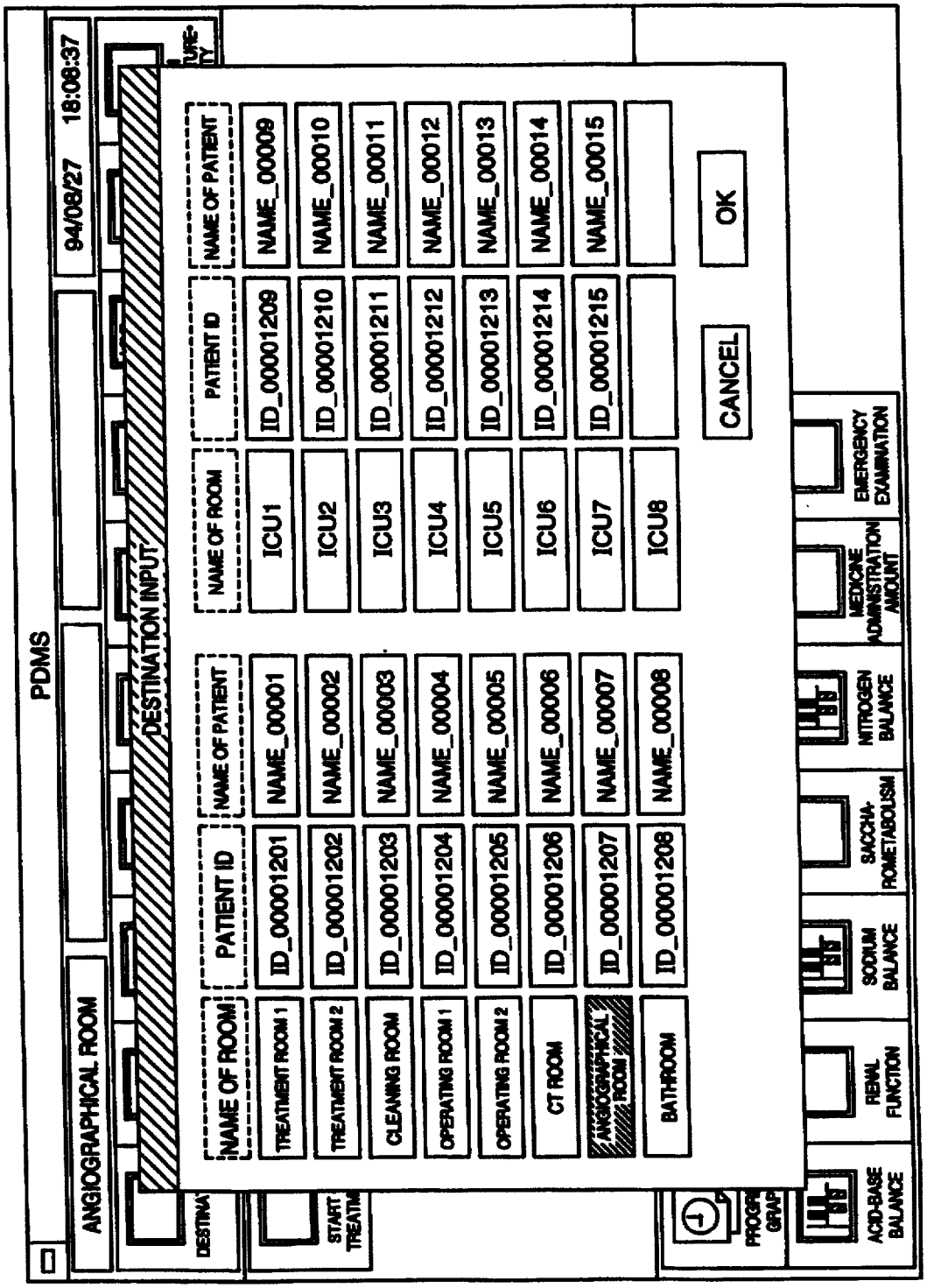
FIG. 12 is a view showing the destination input window of the input terminal according to this embodiment.

This input is made at the reception office 750. The patient attributes are input from the computer 710 in the nurse station (mainly for outpatients). Note that the patient attributes may be input from the input terminal 130 (for emergency patients or the like). In this case, a patient input control procedure is stored in the memory of the input terminal, and an icon for starting a patient information input program or the like is prepared on the initial menu window shown in FIG. 9 (FIG. 9: start of treatment). When this icon is designated for an input, a new patient data record is generated. The current window changes to a patient information input window shown in FIG. 10, and patient attribute input processing is executed.

The patient attributes are given as input items entered by, e.g., a reception clerk or outpatient nurse.

1. Patient ID
2. Name of patient, and reading of its kanji characters
3. Date of birth, age, and sex
4. Height, weight (in good health), body surface area
5. Blood type
6. Past history
7. Race
8. Visiting information Means for visit (A: direct visit by ambulance; B: visit with doctor's letter of introduction; C: others), date of crisis (including estimated date), time of crisis, place of crisis, introduction source, visiting (hospitalization) time data.

The patient attributes are also given as input items entered by a main physician in charge.

1. Name of physician in charge, assistant physician in charge, and name of resident in charge
2. Synoptic department
3. Malady classification and injury classification
4. Exogenic means
5. Symptoms at the time of visit In general, the patient attributes of the main physician in charge are sequentially input after actual examinations and treatments are started.

In the subsequent treatment or examination, when the above patient ID, for example, is input, information to be subsequently transmitted to the server system 800 is identified as patient information represented by the input patient ID. Examination and prescription information for each patient is appropriately recorded.

When this patient arrives at a room where the patient is actually treated, the treatment location is input together with the patient ID and the patient attributes from the input terminal 130 or the like to the server system 800 in step S3. When the patient attributes, the patient ID code, and the like are input, the server system 800 sends patient information and the like to the input source apparatus (e.g., the input terminal or personal computer) to cause the input source apparatus to display the patient information and to prompt confirmation.

In step S4, sensor portions are attached to the patient to collect patient information, necessary medical equipments are started to start collecting the patient information, and sequentially send the collected data to the server system 800. In step S5, patient treatment data is input from the input terminal 130, as needed, and is sent to the server system 800. The input terminal 130 sequentially displays instruction data required in progress of the treatment preset in the server system 800, an input menu window, and the like.

For example, a menu shown in FIG. 9 is displayed in the initial state. The display position of a desired one of various icons displayed on the menu window is designated with an attached pen to easily execute the corresponding processing. The server system 800 receives the patient information in step S6. In step S7, the server system 800 analyzes and formats input data so as to display the pieces of input information from various apparatuses on the display device 115 of each room. In step S8, the analysis result of the information collected from the patient is sent back to the system of the room from which the patient information has been transmitted. For example, this analysis result is sent to the vital information collection apparatus 10 of the treatment room and displayed on the corresponding display device 115.

In the above description, all the collected data are sent from the respective equipments to the server system 800, the server system 800 analyzes these collected data, and the analysis result is sent to the display device 115. The present invention is not limited to this. If the vital information collection apparatus 110 has a function of analyzing collected data, the vital information collection apparatus 110 analyzes the collected data and transmits only necessary data to the server system 800 in a predetermined format. In this case, the collected data in the vital information collection apparatus 110 may be directly sent to the display device 115 and may be displayed thereon. This also applies to other equipments.

Figure 7:
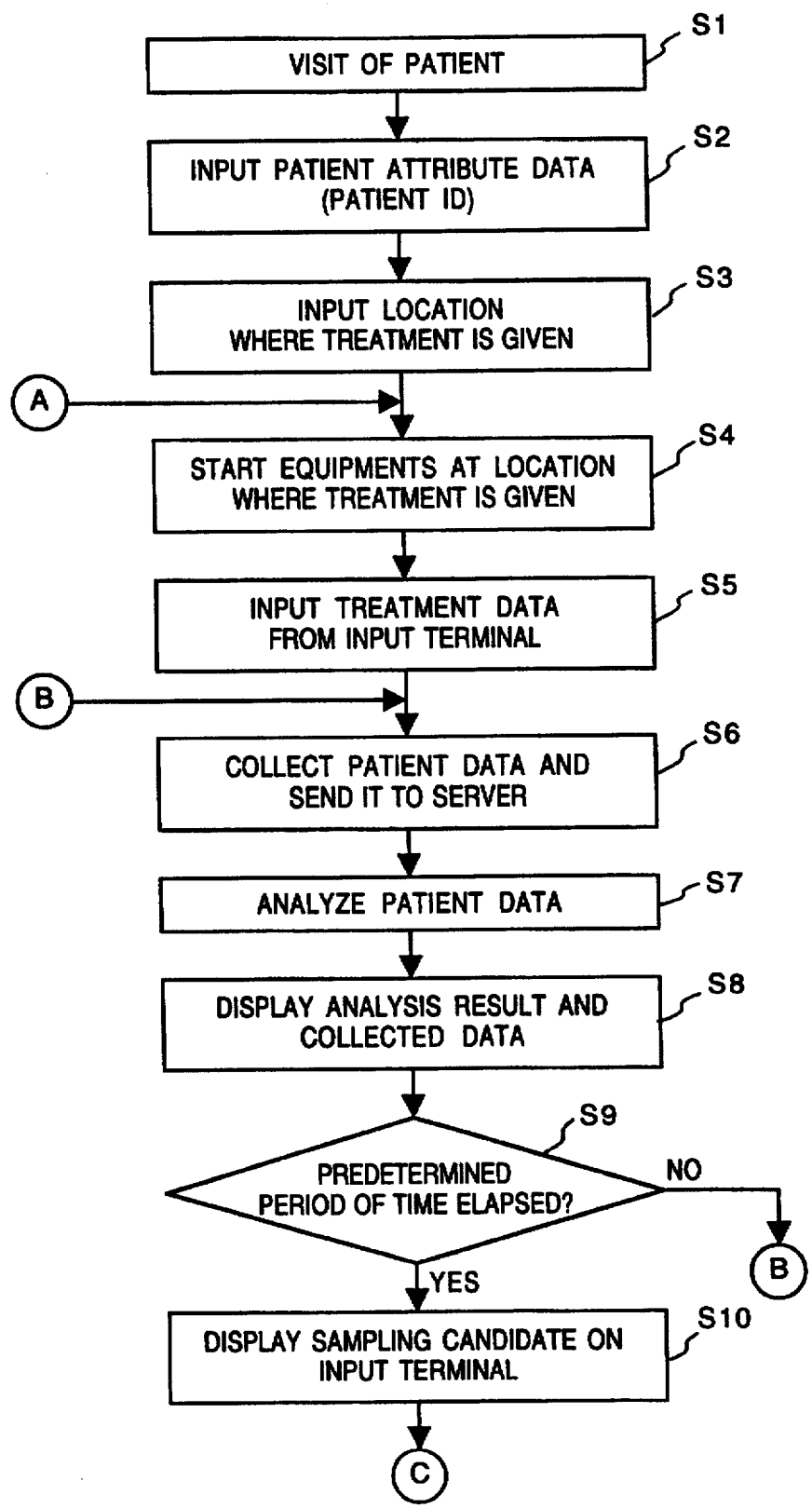
FIG. 7 is a flow chart showing operation control according to this embodiment.
Figure 8:
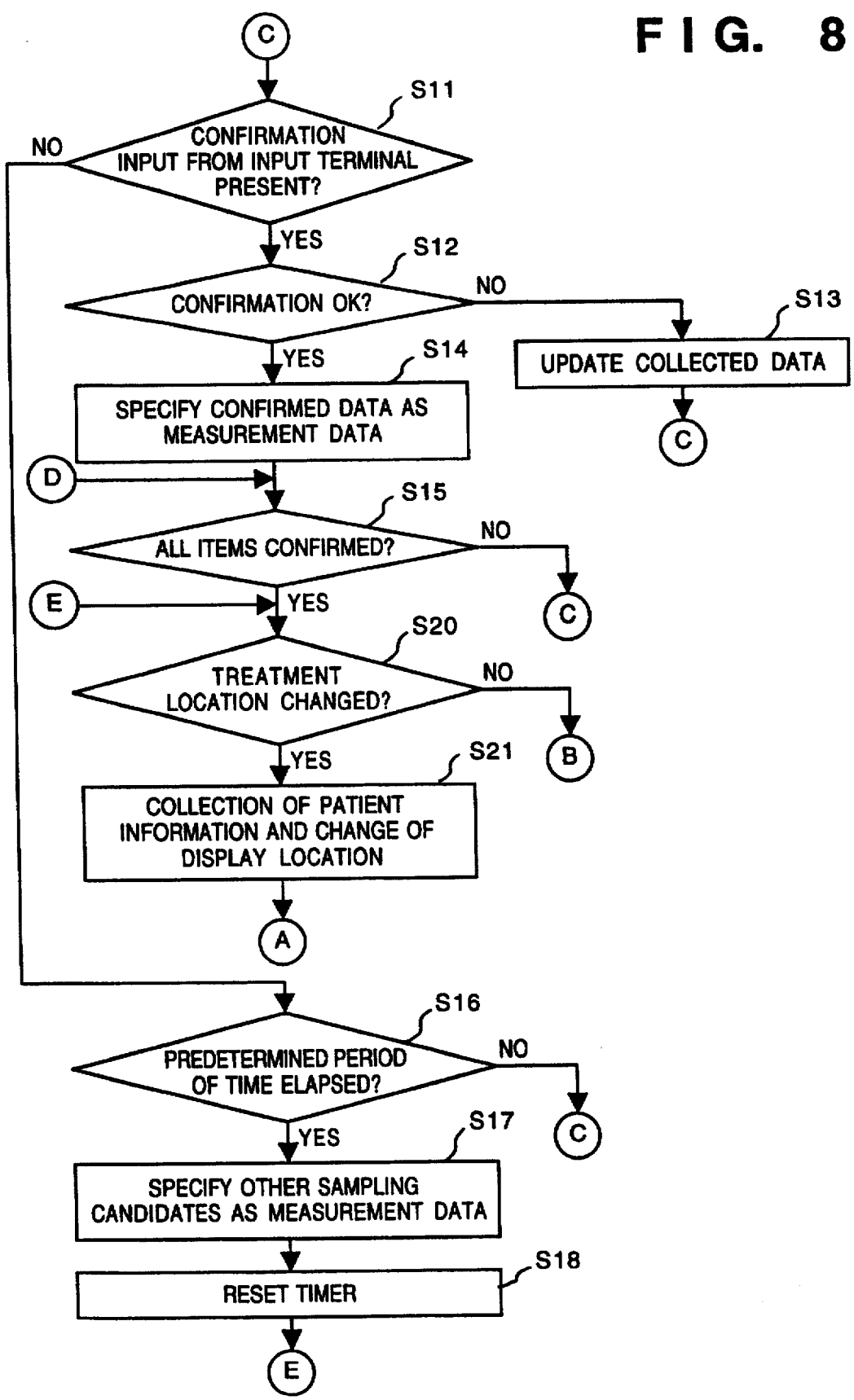
FIG. 8 is a flow chart showing operation control according to this embodiment.

In the processing of FIG. 7, in step S9, the server system 800 processes the data sequentially sent from the patient data collection equipments to determine whether a predetermined preset period of time has elapsed. The purpose of this processing is to collect and record data from the patient every predetermined period of time. For example, during a treatment such as a surgical operation, collected patient data is recorded every 5 minutes. When the predetermined period of time has not yet elapsed, the flow returns from step S9 to step S6, and the above processing is performed until the predetermined period of time elapses.

When the predetermined period of time has elapsed, the flow advances from step S9 to step S10. The server system 800 sends patient data (including analysis result data) to the input terminal 30 at this moment and causes the input terminal 30 to display a message prompting a confirmation input for the patient data. This message and the display layout of the confirmation input window are shown in FIG. 11.

In the example of FIG. 11, confirmation data are HR, PR, RR, APS, APD, T1, T2, SpO2, ICP, and CV as indicated in the item columns. In practice, previously collected data having undergone the confirmation input process are sequentially displayed in the left frames together with the collection times. The collected data are displayed together with sampling times (18:10) between the left frames and the right item columns.

In the illustrated example, neither previously collected data nor currently collected data are present, so that (0.00) is displayed in each item. In practice, however, data collected from the patient are displayed. The previously collected data having undergone the confirmation input process are time-serially displayed in the left frames. The physician can easily check the past and current states of the patient in accordance with the display contents at the input terminal. Relevance determination of the data in the confirmation item can be facilitated.

The server system 800 displaying the collected data on the input terminal 130 as described above determines in step S11 whether a confirmation input from the input terminal is present. If YES in step S11, the flow advances to step S12 to determine whether the confirmation contents are OK or NO. If NO in step S12, the flow advances to step S13. The collected data of the corresponding item is read from the corresponding vital information collection apparatus and is subjected to necessary analysis processing. The processed data is displayed at the corresponding position in the input terminal again. The flow then returns to step S11.

If it is determined in step S11 that the confirmation contents are OK, the flow advances to step S14. The collected data of the item having undergone the confirmation input process is registered in the collected data storage area of the corresponding patient in the storage as the collected data of the corresponding data of the server system 800. The flow then advances to step S15 to determine whether all the confirmation inputs for items to be confirmed are completed. If YES in step S15, the flow advances to step S20.

If NO in step S15, the flow returns to step S11 to prepare for the confirmation input of the next item.

If no confirmation input from the input terminal is present in step S11, the flow advances to step S16 to determine whether a predetermined period of time has elapsed upon the display of the confirmation input window. In this embodiment, this predetermined period of time is defined as one minute. When the predetermined period of time has not yet elapsed, the flow returns to step S11.

When it is determined in step S16 that the predetermined period of time has elapsed, the flow advances to step S17. Of the item data currently displayed on the input terminal, all the data not having undergone the confirmation input process are specified as effective collected data although they are not confirmed yet. The specified data are stored in the collected data storage area of the patient in the server system 800. The display contents of the input terminal are returned to the initial state shown in FIG. 9, and the flow advances to step S20.

It is determined in step S20 whether the treatment for the patient in the current treatment room is completed and the patient is to be moved to the next room. If the treatment must continue in the current treatment room, the flow returns to step S6 to continue the current patient information collection and treatment.

When the above treatment continues and is completed in this room, the patient is moved to another room where a necessary treatment is given to the patient. Alternatively, if all the treatments required for the time being are completed, the patient must be moved to the next room such as an intensive care unit or general ward to receive care.

In this case, the icon "destination" at the upper left of the input terminal is designated. The display of the input terminal is shifted to a destination input menu. The room of the destination is designated from the current room (angiographical room in the illustrated example) displayed in a display form different from others.

In this case, the server system 800 concentratedly manages the information from all the systems. The server system 800 recognizes, as an operative state, a room from which information is sent, or a room or location for which movement of the patient is reserved. If no patient is present in the destination room and no reservation for movement is made for this destination room, the server system 800 recognizes that this room is in an "empty" state and is available for a new patient. When the server system 800 recognizes that a given room is used by a specific patient and data is sent from this room, or when a given room is not currently used, but is reserved as a movement destination, the patient ID and the name of patient are displayed together with the name of this room.

To designate a destination room, a destination at which no patient ID is displayed can be designated as the destination while the destination input window is observed. The control procedure for operating the input terminal and the like are stored in the memory of the terminal, and only an instruction input is sent to the server system 800.

When destination input processing is completed, the system operation in the corresponding room is completed. As a result, the presence of a treatment room change input is detected in step S20, and the flow advances to step S21. Collected data in the destination room are then stored in the storage as data continuous with the data previously collected in the previous treatment room.

After a destination is input, the physician or nurse of the system of this embodiment moves the patient to the destination room. When movement of the patient to the destination room is completed, the destination system is started to collect patient data in the destination room. As a result, patient data is sent together with the patient code of the newly moved patient from the destination system to the server system 800.

When vital information is kept collected during movement, this data is also sent to the server system 800 and can be recorded as continuous data including the data during the movement. In this case, during movement, collected patient data may be transmitted from the patient data collection apparatus to the server system 800 through, e.g., radio or optical communication. Alternatively, the patient data collection apparatus may be arranged to have a patient data storage function. All the patient data obtained during movement may be collectively transmitted upon completion of the movement to the destination.

As described above, according to this embodiment, data collected upon a treatment in each room after the patient visits the hospital can be continuously and time-serially stored. For this reason, even if various treatments are performed for the patient in a plurality of rooms, the vital information and various data collected from this patient can be continuously and time-serially read out and output, thus greatly helping the diagnosis. In addition, the patient data is not unconditionally sampled every predetermined period of time to become effective data. Since sampling is confirmed every predetermined period of time, irrelevant data can be eliminated during collection, and high-precision collected data can be stored. In this case, even if a physician or nurse forgets inputting a confirmation input or is busy in other treatments and unable to perform the confirmation input process, and if no confirmation input is made within a predetermined period of time, the data can be specified as the data collected from the patient, thereby preventing data omissions.

In this embodiment, in addition to the above time-serial collection of the patient data, the result of a treatment for a patient can be input from the input terminal of the room of this patient along with the movement of the patient. Therefore, the treatment state for the patient can be easily confirmed from the server system 800, the nurse station 700, or the like.

Instructions for executing various treatments may be input and registered at the medical office system 600 in advance or upon examination of the patient. The registration contents are displayed on the system of a room where a patient requiring various treatments in accordance with data collection situations is present, and a message representing a specific treatment required for the patient can be given. When this specific treatment is completed, the end of treatment is input from the input terminal, so that the physician or nurse can easily determine the progress of the treatments. Each instruction need not be printed out from the medical office or need not be handwritten. In addition, a necessary instruction for a given treatment can be output from the system of the room in which the given treatment is actually performed without any special operation, as needed.

The instructions for executing various treatments include an infusion and an instruction for adjuvants. An example of the instruction for adjuvants will be described below.

In this case, an instruction file input is made at the nurse station 600 or the medical station 700. An instruction file is prepared in accordance with the following schematic procedures.

1) Input of Patient ID/Bed Number

When a patient ID or a bed number is input, the previously registered patient attributes are displayed. At this time, the previously prepared instruction file is also displayed. When an icon "erase" is selected, the contents are erased to set a new preparation mode. The attributes can be changed, as needed.

2) Selection of Item Category

An input item is selected from the item categories.
① Continuous intravenous infusion
② Continuous intravenous microinfusion
③ Shot medicine
④ Blood transfusion ⑤ Nutrient ⑥ Notes (other item selection inputs for designating a specific symptom, or free inputs). A dictionary for adjuvants for a patient is arranged in advance in a system such as a medical office system for inputting an instruction file. The selection input items to be described below are selected from the ones registered in the dictionary.

For example, when the continuous intravenous infusion is selected as an item category, a continuous intravenous infusion instruction, as shown in FIG. 13, is made. More specifically, a basic infusion is selected from the dictionary, and adjuvants are then selected from the dictionary. An optimal adjuvant pattern is selected from four adjuvant patterns A to D, as shown in FIG. 13. An administration rate instruction is input, and then a start time is input.

When the continuous intravenous microinfusion is selected as an item category, a continuous intravenous microinfusion is instructed from the dictionary. More specifically, a basic medicine is selected, and a solvent is then selected from the dictionary. An administration rate instruction is input, and then a start time is input. When a shot medicine is selected from the item category, a shot medicine is instructed from the dictionary, as shown in FIG. 15. More specifically, a basic medicine is selected from the dictionary, and then a solvent is selected from the dictionary. An administration interval is input, and an administration rate is designated and input, and then a start time is input.

When a nutrient is selected from the item category, a nutrient input instruction is input, as shown in FIG. 16. More specifically, the name of a nutrient is selected from the nutrient dictionary, and a solvent is then selected. In this embodiment, water is set as an initial value, and an adjuvant is designated. In this embodiment, salt is set as the initial value of the adjuvant.

An administration interval is input, and then an administration rate is designated and input. A start time is then input, thereby printing and issuing an instruction file (FIG. 20). Simultaneously, notes are also input.

As a result of the above operations, the instruction file is registered as the treatment instructions for the patient designated in the server system 800. The server system 800 transfers the contents of the registered instruction file to the system of a room where a treatment is being performed for this patient. Therefore, when the instruction file is simply prepared, the instruction contents are properly notified to the location where the designated patient is present.

When the instruction file is input as described above, the instruction contents are sent to the input terminal 130. When the infusion/blood transfusion instruction input icon on the initial window menu shown in FIG. 9 is opened, the instruction contents are displayed. The contents of the instruction file can be properly and quickly confirmed at a location where a treatment is to be performed. A treatment following the instruction file such as an adjuvant treatment using infusion can be performed without any error while the display contents on the display device of the treatment room for this instruction file are checked. A start time for adjuvant administration through the infusion, infusion exchange time, infusion end time, and the like are input from the input terminal of the treatment room by judgment of an operating physician in accordance with this instruction file. Therefore, the server system 800 can concentratedly manage all information associated with the patient.

Figure 17:
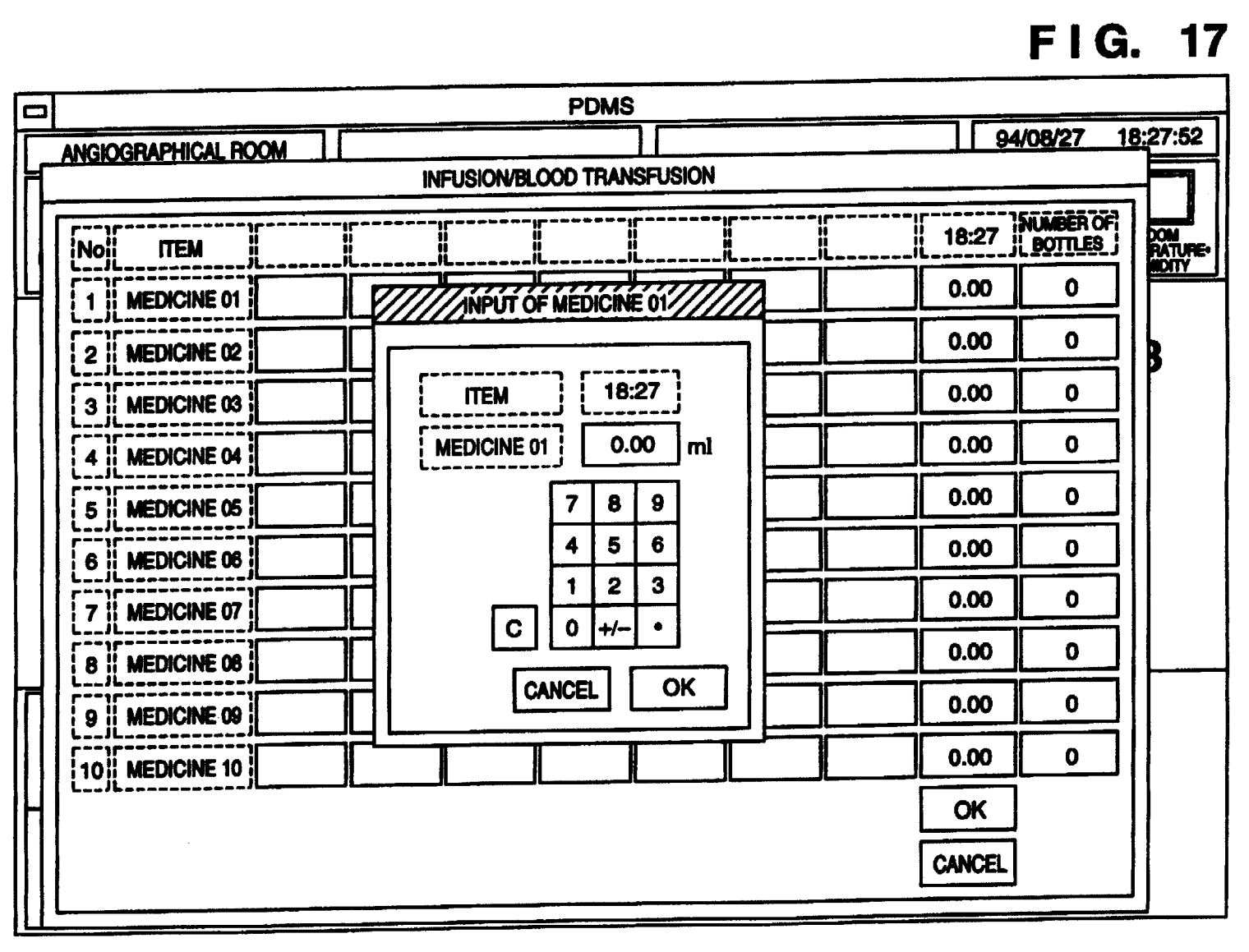

An infusion/blood transfusion input will be described below. The names of medicines administered to the patient are clicked. The input window of the names of medicines is shown in FIG. 17.

Codes corresponding to the names of medicines not designated by the instruction file but registered in the above dictionary can be input at this time. The administered medicines are input with a ten-key pad, and a key "OK" is entered.

Information of adjuvants sequentially administered is designated and input in this manner.

As described above, according to this embodiment, since the continuous treatment process for a patient and the patient state can be detected, the detected result can be easily visually displayed. In consideration of this feature, the patient state and the treatment result can be displayed or printed out along the same time axis. An output example in which the state of a patient and treatments for this patient during a surgical operation are printed out is shown in FIGS. 18A and 18B.

Figure 18A:
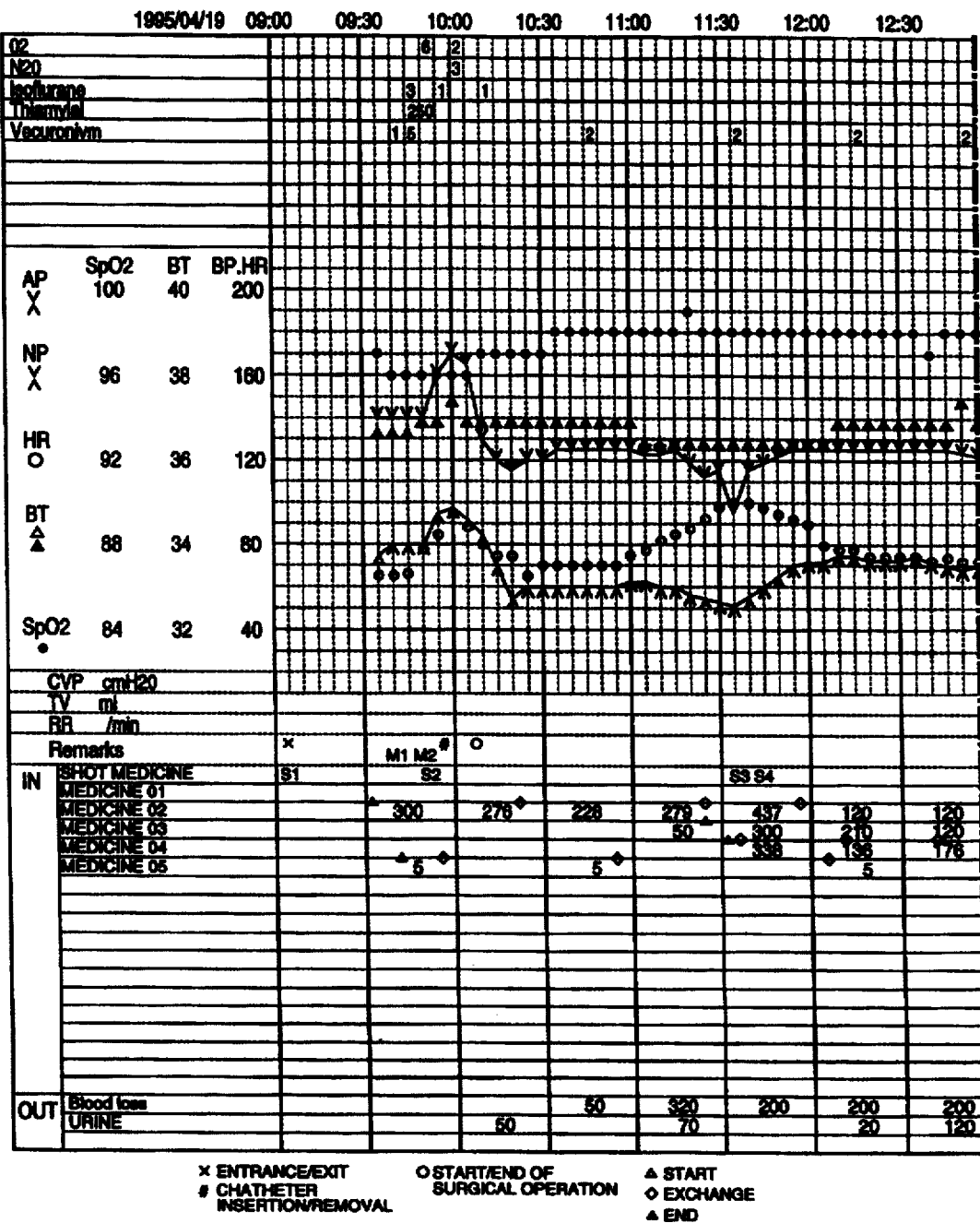
FIGS. 18A and 18B are charts showing patient information outputs in an operating room according to this embodiment.
Figure 18B:
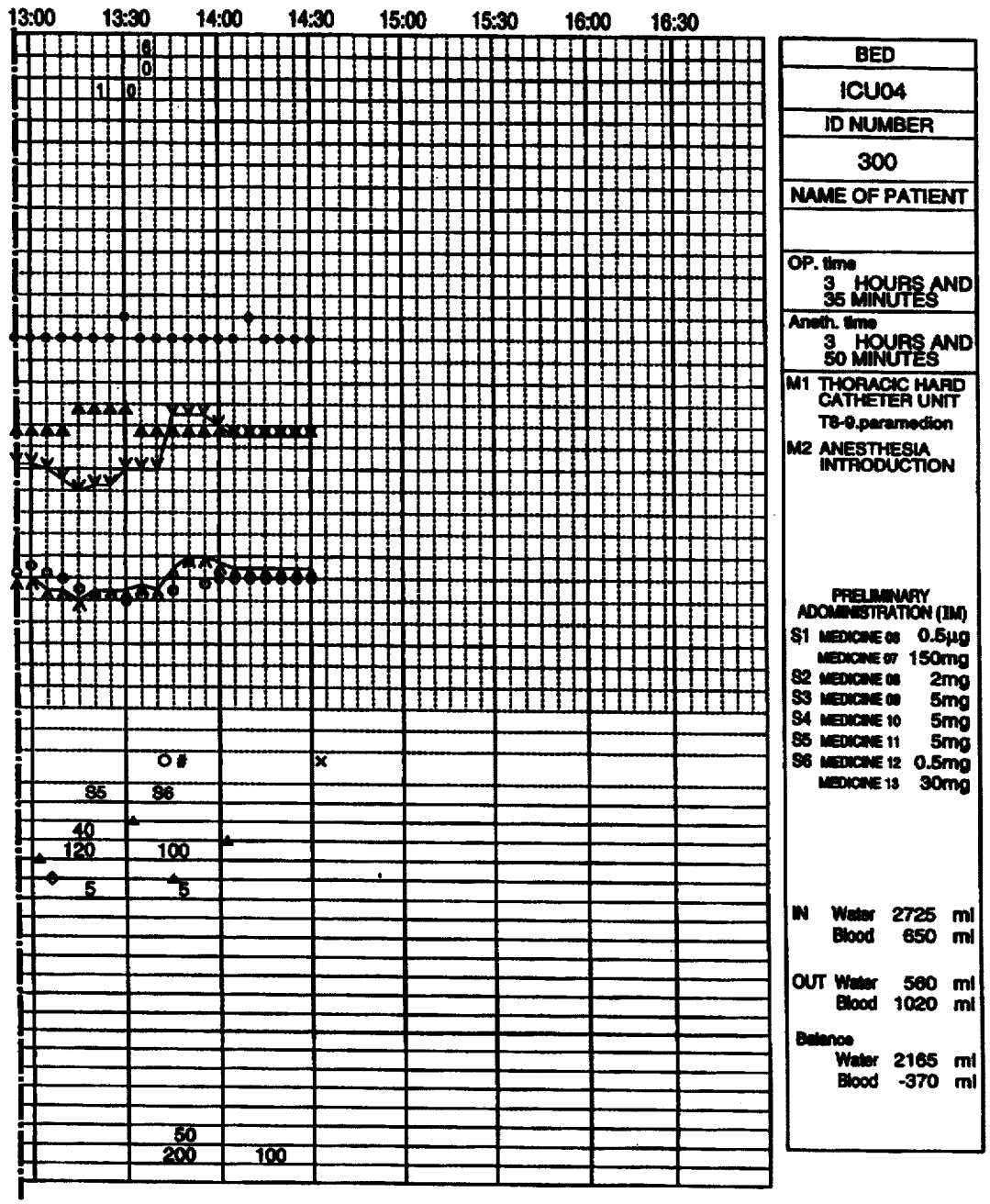

The example in FIGS. 18A and 18B show the printouts from entrance to the operating room to exit therefrom in a series of treatments. This embodiment, however, is not limited to the above example. For example, even if the treatment room changes, the data collected from the patient can be stored in the memory in a time-serially continuous form. For this reason, in the printout state or the display state of the patient information on the display device, the data can be easily read out and formatted.

Figure 19A:
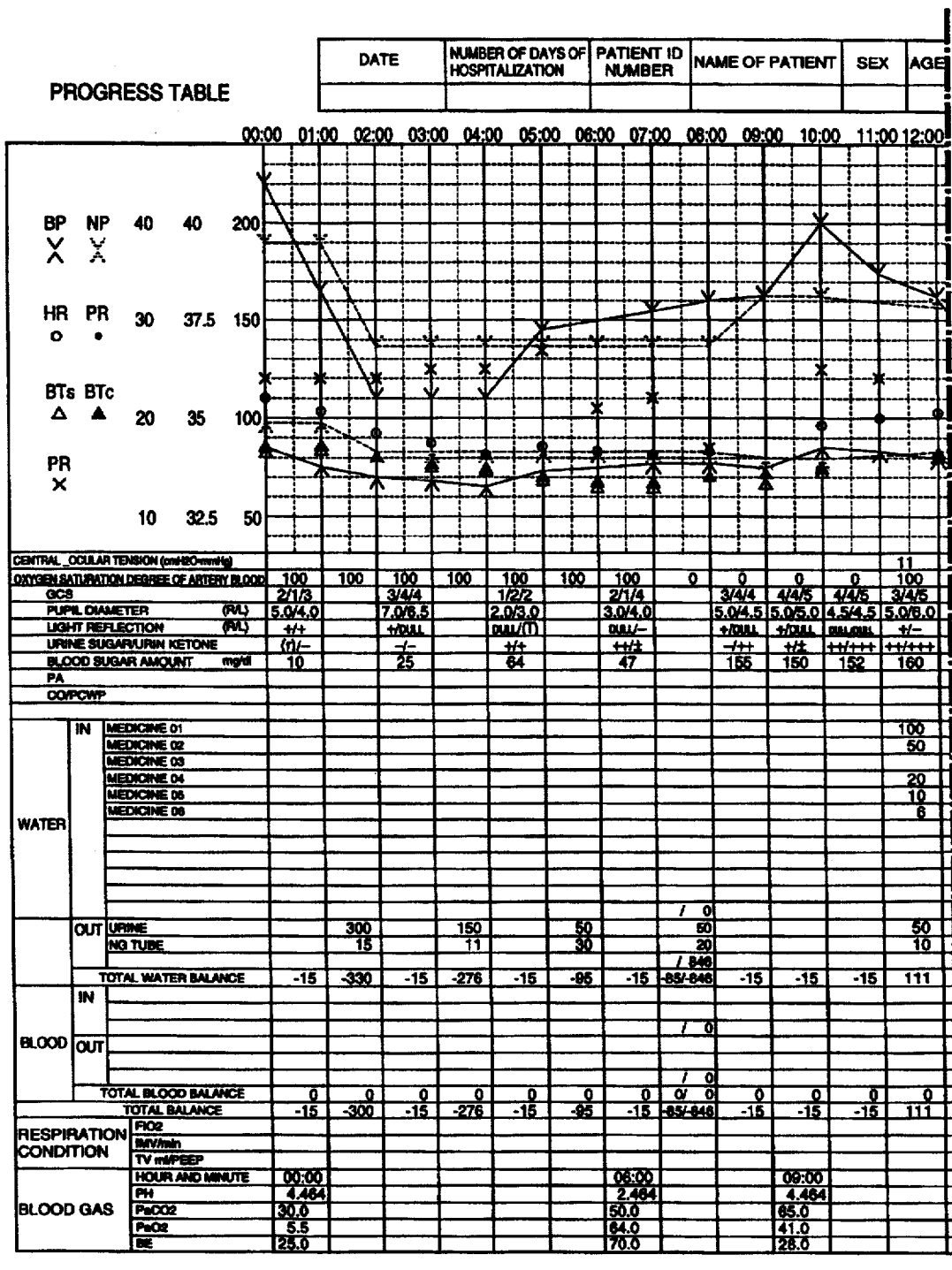
FIGS. 19A and 19B are charts showing 24-hour continuous patient information outputs.
Figure 19B:
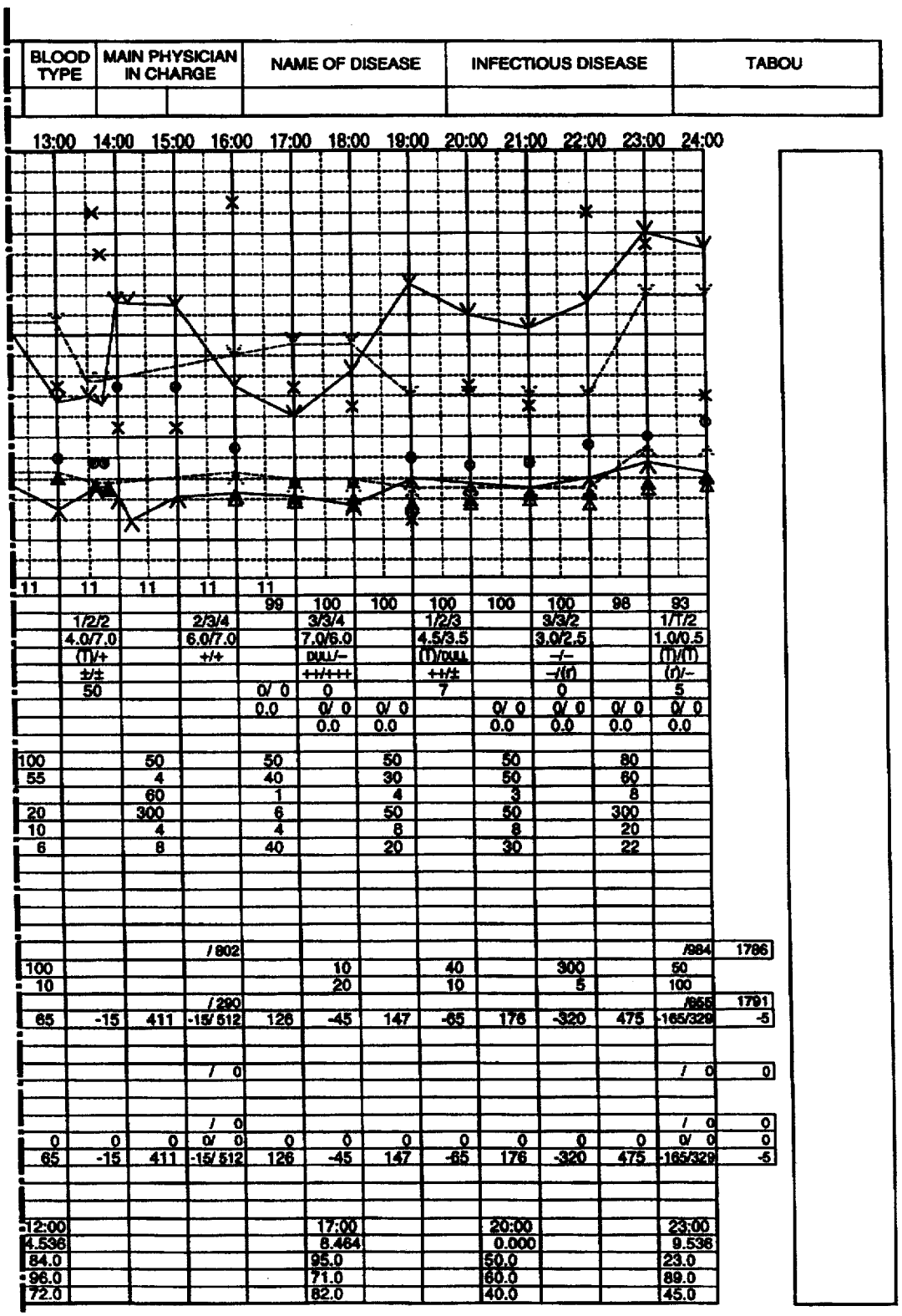

FIGS. 19A and 19B show examples in which the states of collection of the 24-hour continuous patient information and treatments for a patient are printed out along the same time axis. FIGS. 19A and 19B are examples of 24-hour continuous format in which an ICU patient enters the operating room and returns to the ICU.

As shown in FIGS. 18A, 18B, 19A and 19B, according to this embodiment, even if a patient is moved between a plurality of rooms for examinations and the like, the patient information in the respective rooms can be sent to the server system 800 from the systems of rooms in which treatments are sequentially performed. The data collected from the patient can be continuously displayed or printed out. The data from the patient and diagnosis data are simultaneously displayed together with adjuvant information along the same time axis.

According to this embodiment, as described above, patient information and collected data upon movement of a patient are not distributedly stored, but all the information and data can be concentratedly managed as continuous data from entrance to leaving of the hospital, and the processing results can be output.

For example, body fluid balance management such as infusion/blood transfusion, time-serial management and analysis of the correlation between various examinations and vital information, error prevention in giving and receiving an instruction for a treatment, an improvement in nursing due to a reduction of documentation, and the like can be achieved.

As has been described above, according to the present invention, patient information and collected data upon movement of a patient are not distributedly stored, but all the information and data can be concentratedly managed as continuous data from entrance to leaving of the hospital, and the processing results can be output.

For example, body fluid balance management such as infusion/blood transfusion, time-serial management and analysis of the correlation between various examinations and vital information, error prevention in giving and receiving an instruction for a treatment, an improvement in nursing due to a reduction of documentation, and the like can be achieved.

As many apparently widely different embodiments of the present invention can be made without departing from the spirit and scope thereof, it is to be understood that the invention is not limited to the specific embodiments thereof except as defined in the appended claims.

What is claimed is:

1. A patient information analysis management system having a patient information collection apparatus for collecting results of medical treatments given to a patient in plurality of locations at which medical treatments are performed, in a medical facility for performing medical treatments at the plurality of locations, and a server apparatus for collecting and holding information from said patient information collection apparatus, wherein said patient information collection apparatus comprises patient information transmitting means for transmitting the information of the results of the medical treatments taken by the patient to said server apparatus, display means for receiving data transmitted to said server apparatus and displaying the received data on a display device, confirmation means for confirming display contents of said display means to output an instruction representing relevancy of the display contents, and informing means for informing said server apparatus of destination information when the medical treatment for the patient at a given location is completed and the patient moves to a next location, and said server apparatus comprises memory means capable of storing information necessary for medical treatments given to the patient and the results of the medical treatments taken by the patient, analysis return means for analyzing, as needed, the information transmitted from said patient information transmitting means of said patient information collection apparatus and returning an analysis result to said patient information collection apparatus, storage means for storing the information transmitted from said patient information transmitting means of said patient information collection apparatus and the analysis results from said analysis return means in said memory means, patient information control means for exchanging subsequent information associated with the patient with a patient information collection apparatus specified at a destination when the destination of the patient is sent from said informing means of said patient information collection apparatus, and confirmation information control means for accepting or discarding the display information, confirmed by said confirmation means of the patient information collection apparatus, in accordance with the confirmation result.

2. The system according to claim 1, wherein the information sent by said patient information transmitting means of said patient information collection apparatus includes vital information collected from the patient and adjuvant information of the patient.

3. The system according to claim 1, wherein said display means of said patient information collection apparatus can display data collected by said patient information collection apparatus.

4. The system according to claim 1, wherein the data transmitted from said server apparatus includes adjuvant prescription information following an adjuvant prescription to the patient stored in said memory means in advance, and destination input guidance information at said informing means.

5. The system according to claim 1, wherein said analysis return means of said server apparatus extracts patient measurement information for the predetermined period of time from the patient information transmitted from said patient information transmitting means and returns the extracted information as a sampling candidate, and said display means of said patient information collection apparatus displays the sampling candidate from said server apparatus and confirms storable information as measurement information from the sampling candidate information displayed on said display means.

6. The system according to claim 5, wherein when said confirmation means instructs that the sampling candidate is irrelevant, said analysis return means of the server apparatus extracts new patient measurement information of the patient information transmitted from said patient information transmitting means and returns the new patient measurement information as a sampling candidate, and said display means of said patient information collection apparatus displays the sampling candidate retransmitted from said server apparatus, and said confirmation means checks if the retransmitted sampling candidate information displayed on said display means is storable information.

7. The system according to claim 5, wherein when said confirmation means does not perform a confirmation operation for the predetermined period of time, the displayed sampling candidate is specified as the storable measurement information.

8. A patient information analysis management method in a patient information analysis management system having a patient information collection apparatus for collecting results of medical treatments given to a patient in a plurality of locations at which medical treatments are performed, in a medical facility for performing medical treatments at the plurality of locations, and a server apparatus for collecting and holding information from the patient information collection apparatus, comprising causing said patient information collection apparatus to send a medical treatment result of the patient to said server apparatus, and causing said server apparatus to extract, from all patient information of the sent information, patient measurement information obtained every predetermined period of time and to return extracted information as a sampling candidate to said patient information collection apparatus, causing said patient information collection apparatus to display sampling candidates from said server apparatus and to confirm whether of all the displayed sampling candidate information, storable information is relevant as the measurement information, and when a confirmation result is relevant, causing said server apparatus to store the confirmed patient information as the measurement information of the patient, and when the confirmation result is irrelevant, extracting a sampling candidate again and returning the sampling candidate to said patient information collection apparatus.

9. The method according to claim 8, further comprising specifying the displayed sampling candidate as storable measurement information when confirmation is not performed for a predetermined period of time.

* * * * *